US010710002B2

(12) United States Patent
Sun et al.

(10) Patent No.: US 10,710,002 B2
(45) Date of Patent: Jul. 14, 2020

(54) METHOD OF EXTRACTING NUTRIENTS FROM A PLANT

(71) Applicant: NUECOLOGY BIOMEDICAL INC., Richmond, B.C. (CA)

(72) Inventors: Chung-Chin Sun, Richmond (CA); Yeuh-Hui Lin, Pingtung (TW); Shan-Shue Wang, Tainan (TW)

(73) Assignee: NUECOLOGY BIOMEDICAL INC., Richmond (CA)

( * ) Notice: Subject to any disclaimer, the term of this patent is extended or adjusted under 35 U.S.C. 154(b) by 667 days.

(21) Appl. No.: 15/407,928

(22) Filed: Jan. 17, 2017

(65) Prior Publication Data

US 2017/0216739 A1    Aug. 3, 2017

(30) Foreign Application Priority Data

Feb. 2, 2016    (CN) .......................... 2016 1 0072875

(51) Int. Cl.
| | |
|---|---|
| *A61K 36/00* | (2006.01) |
| *B01D 3/14* | (2006.01) |
| *C07D 307/62* | (2006.01) |
| *C07C 227/40* | (2006.01) |
| *C07D 307/84* | (2006.01) |
| *C07C 51/44* | (2006.01) |
| *C07D 311/04* | (2006.01) |
| *B01D 3/00* | (2006.01) |
| *B01D 11/02* | (2006.01) |
| *C07C 45/82* | (2006.01) |
| *C07C 67/54* | (2006.01) |

(52) U.S. Cl.
CPC ............. *B01D 3/143* (2013.01); *B01D 3/001* (2013.01); *B01D 11/02* (2013.01); *C07C 45/82* (2013.01); *C07C 51/44* (2013.01); *C07C 67/54* (2013.01); *C07C 227/40* (2013.01); *C07D 307/62* (2013.01); *C07D 307/84* (2013.01); *C07D 311/04* (2013.01)

(58) Field of Classification Search
None
See application file for complete search history.

(56) References Cited

U.S. PATENT DOCUMENTS 5,494,668 A * 2/1996 Patwardhan .......... A61K 36/324
424/756
5,494,688 A * 2/1996 Rebstock ................ A23P 20/10
426/102

OTHER PUBLICATIONS

Yalavarthi et al. (2013) Int. J. Res. Pharm. Sci. 4(2): 123-140. (Year: 2013).*
Raskin et al. (2004) Current Pharmaceutical Design 10, 3419-3429. (Year: 2004).*
Revilla et al. (1998) J. Agric. Food Chem. 46: 4592-4597. (Year: 1998).*
Romanick et al. (2007) J. Biochem. Biophys. Methods 70: 253-261. (Year: 2007).*
Azmir et al. (2013) Journal of Food Engineering 117: 426-436. (Year: 2013).*

* cited by examiner

*Primary Examiner* — Terry A McKelvey
*Assistant Examiner* — Russell G Fiebig
(74) *Attorney, Agent, or Firm* — Hamre, Schumann, Mueller & Larson, P.C.

(57) ABSTRACT

A method of extracting nutrients from a plant includes the steps of: pulverizing a water soluble nutrient-based plant part of a first plant material of the plant so as to form a first pulverized plant part; pulverizing a lipid soluble nutrient-based plant part of a second plant material of the plant so as to form a second pulverized plant part; subjecting the first pulverized plant part to a distillation so as to obtain a distillate and a first residue that contains a water soluble nutrient; and immersing the second pulverized plant part in the distillate to form a first mixture followed by distillation of the first mixture, so as to obtain a second residue that contains a lipid soluble nutrient.

17 Claims, 1 Drawing Sheet

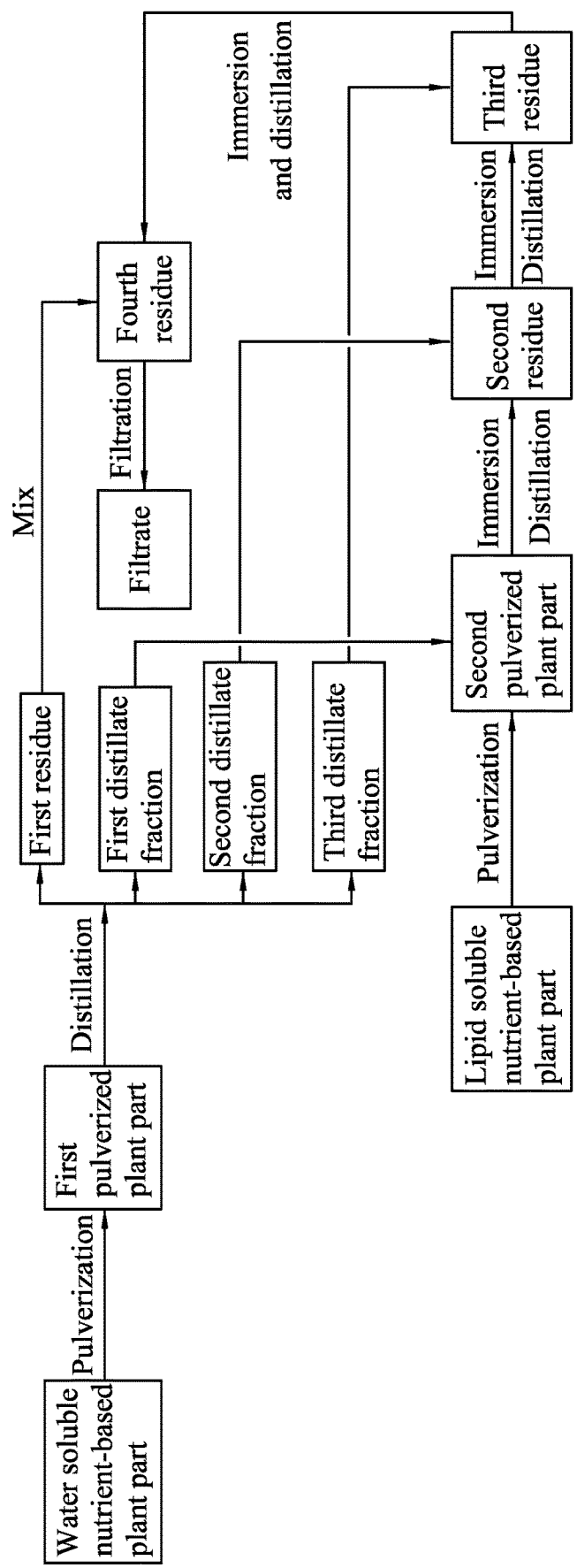

METHOD OF EXTRACTING NUTRIENTS FROM A PLANT

CROSS-REFERENCE TO RELATED APPLICATION

This application claims priority of Chinese Patent Application No. 201610072875.1, filed on Feb. 2, 2016.

FIELD

The disclosure relates to a method of extracting nutrients from a plant.

BACKGROUND

A common goal pursued by researchers in the field of plant extraction, particularly those in academia, government, and industry alike, is to be able to efficiently and effectively extract and produce high yields of nutrients naturally present in various parts of the plants (such as the seeds, roots, stems, leaves and fruits) and to optimize the conditions of extraction (such as mass transfer and heat transfer) for large scale production of the nutrients. Currently, nutrients such as polyphenols, polysaccharides, vitamins, and flavonoids, as well as antibacterial agents and natural pigments, etc., found in plants can be extracted with advanced physical and chemical techniques or by using biotechnology equipment. These extracted nutrients can be formulated into healthcare and pharmaceutical products for oral administration or external application that promote effects such as anti-oxidation, anti-aging and anti-inflammation.

For instance, vitamins are essential nutrients required by organisms to orchestrate a range of physiological functions, and thus a deficiency of vitamins could lead to serious health problems. Therefore, cosmetic, pharmaceutical and healthcare products are increasingly being supplemented with various functional vitamins.

Since vitamins cannot be synthesized by the human body, they must be obtained through the diet (such as vegetable and fruit). In addition, vitamins can also be directly extracted from the diet with organic solvents or produced through chemical synthesis. However, the organic solvents used in these methods are not energy-efficient and environmentally-friendly, and could harm the human body and inhibit the body's ability to absorb nutrients. The purification process to reduce the levels of residual solvents is thus needed, but is relatively time and cost consuming.

Therefore, the applicants have endeavored to develop a method of obtaining nutrients naturally, without the need for addition of organic solvents.

SUMMARY

Therefore, an object of the disclosure is to provide a method of extracting nutrients from a plant that can alleviate at least one of the drawbacks of the prior art.

According to the disclosure, the method includes the steps of:

pulverizing a water soluble nutrient-based plant part of a first plant material of the plant so as to form a first pulverized plant part;

pulverizing a lipid soluble nutrient-based plant part of a second plant material of the plant so as to form a second pulverized plant part;

subjecting the first pulverized plant part to a distillation so as to obtain a distillate and a first residue that contains a water soluble nutrient; and immersing the second pulverized plant part in the distillate to form a first mixture followed by distillation of the first mixture, so as to obtain a second residue that contains a lipid soluble nutrient.

BRIEF DESCRIPTION OF THE DRAWING

Other features and advantages of the disclosure will become apparent in the following detailed description of the embodiments with reference to the accompanying drawing, of which:

FIG. 1 is a flow chart illustrating an embodiment of a method of extracting nutrients from a plant according to the disclosure.

DETAILED DESCRIPTION

Referring to FIG. 1, an embodiment of a method of extracting nutrients from a plant according to the disclosure includes the following steps:

pulverizing a water soluble nutrient-based plant part of a first plant material of the plant so as to form a first pulverized plant part;

pulverizing a lipid soluble nutrient-based plant part of a second plant material of the plant so as to form a second pulverized plant part;

subjecting the first pulverized plant part to a distillation so as to obtain a distillate and a first residue that contains a water soluble nutrient; and immersing the second pulverized plant part in the distillate to form a first mixture followed by distillation of the first mixture, so as to obtain a second residue that contains a lipid soluble nutrient.

In certain embodiments, the first plant material and the second plant material may be the same or different plant material (such as root, stem, leaf, seed and fruit). Examples of the plant material of the plant include, but are not limited to, the berry of Sea Buckthorn, the rhizome of *Curcuma longa* L., the root of *Salvia miltiorrhiza*, the seed of *Bixa orellana*, the leaf of *Camellia sinensis*, and the lemon of *Citrus depressa* Hayata.

In certain embodiments, the first plant material and the second plant material are the same plant material, and the water soluble nutrient-based plant part and the lipid soluble nutrient-based plant part are derived from different parts of the plant material. In certain embodiments, these plant parts may be fresh parts or to-be-discarded parts that either have been used, can be used but have poor quality, or cannot be used.

In certain embodiments, the first pulverized plant part may be formed by pulverizing at least two different kinds of water soluble nutrient-based plant parts which may be from the same or different plant materials. Similarly, the second pulverized plant part may be formed by pulverizing at least two different kinds of lipid soluble nutrient-based plant parts which may be from the same or different plant materials.

In certain embodiments, the water soluble nutrient may be, but not limited to, vitamin C, γ-aminobutyric acid, salvianolic acid, norbixin, catechin, citric acid, anthocyanidin, or combinations thereof. According to the disclosure, the step of pulverizing the water soluble nutrient-based plant part aims to increase the surface area of the first pulverized plant part, so that the efficiency of subsequent distillation steps may be improved. In certain embodiments, the first pulverized plant part has an average particle size ranging from 75 μm to 125 μm.

In certain embodiments, the lipid soluble nutrient may be, but not limited to, vitamin E, curcumin, tashinone, phytosterol, chlorophyll, or combinations thereof. According to the disclosure, the step of pulverizing the lipid soluble nutrient-based plant part aims to increase the surface area of the second pulverized plant part, so as to increase the yield of the lipid soluble nutrient. In certain embodiments, the second pulverized plant part has an average particle size ranging from 50 μm to 100 μm.

In certain embodiments, the step of distilling the first pulverized plant part is conducted at a pressure ranging from 0.01 Kpa to 202.2 Kpa, preferably under vacuum. According to the disclosure, the distillate thus formed may include different distillate fractions that were obtained by distilling the first pulverized plant part at different temperatures. In an embodiment of the disclosure, the distillate includes a first distillate fraction, and, in the immersing step, the second pulverized plant part is immersed in the first distillate fraction.

In another embodiment of the disclosure, the distillate may further include a second distillate fraction that is obtained by distilling the first pulverized plant part at a temperature different from that at which the first pulverized plant part was distilled for obtaining the first distillate fraction. In this embodiment, the method further includes the step of immersing the second residue in the second distillate fraction to form a second mixture followed by distillation of the second mixture, so as to obtain a third residue that contains a lipid soluble nutrient.

In yet another embodiment of the disclosure, the distillate further includes a third distillate fraction that is obtained by distilling the first pulverized plant part at a temperature different from those at which the first pulverized plant part was distilled for obtaining the first and second distillate fractions. In this embodiment, the method further includes the step of immersing the third residue in the third distillate fraction to form a third mixture followed by distillation of the third mixture, so as to obtain a fourth residue that contains a lipid soluble nutrient.

In certain embodiments, the temperature for obtaining the third distillate fraction is higher than that for obtaining the second distillate fraction, and the temperature for obtaining the second distillate fraction is higher than that for obtaining the first distillate fraction. The temperature for obtaining the first distillate fraction may be lower than 50° C., so that the first distillate fraction may contain alcohols (such as methanol and ethanol). The temperature for obtaining the second distillate fraction may be not less than 50° C. and lower than 70° C., so that the second distillate fraction may contain esters (such as ethyl acetate). The temperature for obtaining the third distillate fraction may range from 70° C. to 90° C., so that the third distillate fraction may contain acids (such as formic acid and acetic acid). These polar compounds (i.e., alcohols, esters and acids) of the distillate may increase the compatibility between the distillate and the lipid soluble nutrient, so as to effectively extract the lipid soluble nutrient from the second pulverized plant part.

In certain embodiments, the method may further include the step of fermenting the first pulverized plant part before the step of subjecting the first pulverized plant part to the distillation. The fermenting step would make the first pulverized plant part to produce more polar compounds so as to obtain the distillate having more polar compounds in the subsequent distillation step. In certain embodiments, the fermenting step is conducted at a temperature ranging from 10° C. to 50° C. for 12 hours to 360 hours.

In certain embodiments, the step of immersing the second pulverized plant part in the first distillate fraction is conducted for 2 hours to 48 hours, and distillation of the first mixture is conducted for 0.5 hours to 10 hours. In certain embodiments, the step of immersing the second pulverized plant part in the first distillate fraction is conducted at a temperature ranging from 5° C. to 40° C., and distillation of the first mixture is conducted at a temperature ranging from 40° C. to 70° C.

In certain embodiments, the step of immersing the second residue in the second distillate fraction is conducted for 1 hour to 48 hours, and distillation of the second mixture is conducted for 0.5 hours to 6 hours. In certain embodiments, the step of immersing the second residue in the second distillate fraction is conducted at a temperature ranging from 5° C. to 60° C., and distillation of the second mixture is conducted at a temperature ranging from 50° C. to 80° C.

In certain embodiments, the step of immersing the third residue in the third distillate fraction is conducted for 1 hour to 12 hours, and distillation of the third mixture is conducted for 0.5 hours to 6 hours. In certain embodiments, the step of immersing the third residue in the third distillate fraction is conducted at a temperature ranging from 20° C. to 75° C., and distillation of the third mixture is conducted at a temperature ranging from 60° C. to 90° C.

According to the disclosure, the method may further include the step of mixing the residues thus obtained followed by filtration to obtain a filtrate containing the water soluble nutrient and the lipid soluble nutrient. In certain embodiments, the filtrate may be obtained by mixing the first residue and the second residue followed by filtration. In certain embodiments, the filtrate may be obtained by mixing the first residue and the third residue followed by filtration. In certain embodiments, the filtrate may be obtained by mixing the first residue and the fourth residue followed by filtration. The mixing step may be conducted at a temperature ranging from 5° C. to 50° C. for 4 hours to 120 hours.

The operating conditions for the immersion, distillation and mixing (such as the temperature and the time period) will vary depending on the plant part to be extracted and the nutrient amount to be obtained, so as to achieve the desired extraction efficiency and prevent the denaturation of the second pulverized plant part.

In certain embodiments, when extracting the nutrients from the berry of Sea Buckthorn, in which pulp and pericarp are used as the water soluble nutrient-based plant part and seed is used as the lipid soluble nutrient-based plant part, the step of immersing the second pulverized plant part in the first distillate is conducted at a temperature ranging from 10° C. to 60° C. for 0.5 hours to 5 hours, and the distillation of the first mixture is conducted at a temperature ranging from 40° C. to 90° C. for 0.5 hours to 5 hours. In the case where the first pulverized plant part is distilled at different temperatures to obtain the first, second and third distillation fractions, the step of immersing the second pulverized plant part in the first distillate fraction is conducted at a temperature ranging from 20° C. to 40° C. for 4 hours to 12 hours, and distillation of the first mixture is conducted at a temperature ranging from 40° C. to 60° C. for 1 hour to 3 hours. The step of immersing the second residue in the second distillate fraction is conducted at a temperature ranging from 25° C. to 40° C. for 1 hour to 6 hours, and distillation of the second mixture is conducted at a temperature ranging from 50° C. to 75° C. for 0.5 hours to 5 hours. The step of immersing the third residue in the third distillate fraction is conducted at a temperature ranging from 25° C. to 60° C. for 1 hour to 6 hours, and distillation of the third mixture is conducted at a temperature ranging from 75° C. to 90° C. for 0.5 hours to 3 hours. The mixing step is conducted at a temperature ranging from 20° C. to 40° C. for 4 hours to 12 hours.

In certain embodiments, when extracting the nutrients from the rhizome of Curcuma longa L., in which main rhizome is used as the water soluble nutrient-based plant part, and lateral shoots of the rhizome (i.e., branch of the rhizome) are used as the lipid soluble nutrient-based plant part, the step of immersing the second pulverized plant part in the first distillate is conducted at a temperature ranging from 20° C. to 40° C. for 4 hours to 48 hours, and the distillation of the first mixture is conducted at a temperature ranging from 40° C. to 85° C. for 0.5 hours to 6 hours. In the case where the first pulverized plant part is distilled at different temperatures to obtain the first, second and third distillation fractions, the step of immersing the second pulverized plant part in the first distillate fraction is conducted at a temperature ranging from 20° C. to 40° C. for 12 hours to 48 hours, and distillation of the first mixture is conducted at a temperature ranging from 40° C. to 60° C. for 1 hour to 5 hours. The step of immersing the second residue in the second distillate fraction is conducted at a temperature ranging from 20° C. to 40° C. for 4 hours to 12 hours, and distillation of the second mixture is conducted at a temperature ranging from 50° C. to 75° C. for 1 hour to 6 hours. The step of immersing the third residue in the third distillate fraction is conducted at a temperature ranging from 20° C. to 400° C. for 6 hours to 12 hours, and distillation of the third mixture is conducted at a temperature ranging from 60° C. to 85° C. for 0.5 hours to 6 hours. The mixing step is conducted at a temperature ranging from 20° C. to 40° C. for 6 hours to 24 hours.

In certain embodiments, when extracting the nutrients from the root of Salvia miltiorrhiza, in which the epidermis of the root is used as the water soluble nutrient-based plant part, and the root without the epidermis is used as the lipid soluble nutrient-based plant part, the step of immersing the second pulverized plant part in the first distillate is conducted at a temperature ranging from 5° C. to 75° C. for 1 hour to 48 hours, and the distillation of the first mixture is conducted at a temperature ranging from 40° C. to 90° C. for 0.5 hours to 5 hours. In the case where the first pulverized plant part is distilled at different temperatures to obtain the first, second and third distillation fractions, the step of immersing the second pulverized plant part in the first distillate fraction is conducted at a temperature ranging from 5° C. to 25° C. for 12 hours to 48 hours, and distillation of the first mixture is conducted at a temperature ranging from 40° C. to 60° C. for 0.5 hours to 3 hours. The step of immersing the second residue in the second distillate fraction is conducted at a temperature ranging from 5° C. to 20° C. for 4 hours to 12 hours, and distillation of the second mixture is conducted at a temperature ranging from 50° C. to 70° C. for 0.5 hours to 3 hours. The step of immersing the third residue in the third distillate fraction is conducted at a temperature ranging from 25° C. to 75° C. for 1 hour to 6 hours, and distillation of the third mixture is conducted at a temperature ranging from 70° C. to 90° C. for 0.5 hours to 3 hours. The mixing step is conducted at a temperature ranging from 5° C. to 40° C. for 12 hours to 48 hours.

In certain embodiments, when extracting the nutrients from the seed of Bixa orellana, in which the seed without aril is used as the water soluble nutrient-based plant part, and the aril of the seed is used as the lipid soluble nutrient-based plant part, the step of immersing the second pulverized plant part in the first distillate is conducted at a temperature ranging from 25° C. to 75° C. for 1 hour to 24 hours, and the distillation of the first mixture is conducted at a temperature ranging from 40° C. to 90° C. for 1 hour to 24 hours. In the case where the first pulverized plant part is distilled at different temperatures to obtain the first, second and third distillation fractions, the step of immersing the second pulverized plant part in the first distillate fraction is conducted at a temperature ranging from 25° C. to 40° C. for 12 hours to 24 hours, and distillation of the first mixture is conducted at a temperature ranging from 40° C. to 600° C. for 1 hour to 4 hours. The step of immersing the second residue in the second distillate fraction is conducted at a temperature ranging from 25° C. to 50° C. for 1 hour to 12 hours, and distillation of the second mixture is conducted at a temperature ranging from 50° C. to 70° C. for 1 hour to 2 hours. The step of immersing the third residue in the third distillate fraction is conducted at a temperature ranging from 25° C. to 75° C. for 1 hour to 6 hours, and distillation of the third mixture is conducted at a temperature ranging from 60° C. to 90° C. for 1 hour to 6 hours. The mixing step is conducted at a temperature ranging from 20° C. to 40° C. for 4 hours to 12 hours.

In certain embodiments, when extracting the nutrients from the leaf of Camellia sinensis var. assamica, in which the leaf without petiole and vein is used as the water soluble nutrient-based plant part, and the petiole and vein of the leaf are used as the lipid soluble nutrient-based plant part, the first pulverized plant part (preferably having an average particle size ranging from 50 µm to 75 µm) may be optionally subjected to fermentation under a suitable condition (such as at 40° C. for 120 hours) before distillation. The step of immersing the second pulverized plant part in the first distillate is conducted at a temperature ranging from 20° C. to 50° C. for 6 hours to 48 hours, and distillation of the first mixture is conducted at a temperature ranging from 40° C. to 80° C. for 1 hour to 10 hours. In the case where the first pulverized plant part is distilled at different temperatures to obtain the first, second and third distillation fractions, the step of immersing the second pulverized plant part in the first distillate fraction is conducted at a temperature ranging from 20° C. to 40° C. for 12 hours to 24 hours, and distillation of the first mixture is conducted at a temperature ranging from 40° C. to 60° C. for 1 hour to 5 hours. The step of immersing the second residue in the second distillate fraction is conducted at a temperature ranging from 20° C. to 40° C. for 12 hours to 48 hours, and distillation of the second mixture is conducted at a temperature ranging from 50° C. to 70° C. for 2 hours to 6 hours. The step of immersing the third residue in the third distillate fraction is conducted at a temperature ranging from 25° C. to 50° C. for 6 hours to 12 hours, and distillation of the third mixture is conducted at a temperature ranging from 60° C. to 80° C. for 1 hour to 5 hour. The mixing step is conducted at a temperature ranging from 20° C. to 40° C. for 4 hours to 24 hours.

In certain embodiments, the lemon of Citrus depressa Hayata, that is to be discarded after squeezing juice therefrom, is used in the method of extracting the nutrients of this disclosure, in which the pericarp and pulp are used as the water soluble nutrient-based plant part, and the seed is used as the lipid soluble nutrient-based plant part. The first pulverized plant part (preferably having an average particle size ranging from 75 µm to 125 µm) may be optionally subjected to fermentation under a suitable condition (such as at 25° C. for 360 hours) before distillation. The step of immersing the second pulverized plant part in the first distillate is conducted at a temperature ranging from 25° C. to 75° C. for 2 hours to 12 hours, and distillation of the first mixture is conducted at a temperature ranging from 50° C. to 90° C. for 2 hours to 10 hours. In the case where the first pulverized plant part is distilled at different temperatures to obtain the first, second and third distillation fractions, the step of immersing the second pulverized plant part in the first distillate fraction is conducted at a temperature ranging from 25° C. to 40° C. for 2 hours to 12 hours, and distillation of the first mixture is conducted at a temperature ranging from 50° C. to 70° C. for 2 hours to 5 hours. The step of immersing the second residue in the second distillate fraction is conducted at a temperature ranging from 25° C. to 60° C. for 6 hours to 12 hours, and distillation of the second mixture is conducted at a temperature ranging from 60° C. to 80° C. for 4 hours to 6 hours. The step of immersing the third residue in the third distillate fraction is conducted at a temperature ranging from 25° C. to 75° C. for 2 hours to 12 hours, and distillation of the third mixture is conducted at a temperature ranging from 70° C. to 90° C. for 2 hours to 4 hours. The mixing step is conducted at a temperature ranging from 25° C. to 50° C. for 4 hours to 24 hours.

The disclosure will be further described by way of the following examples. However, it should be understood that the following examples are solely intended for the purpose of illustration and should not be construed as limiting the disclosure in practice.

EXAMPLES

Experimental Materials:
1. The berry of Sea buckthorn was obtained from Chilliwack, British Columbia, Canada.
2. The rhizome of *Curcuma longa* L. was obtained from Florida, USA.
3. The root of *Salvia miltiorrhiza* was obtained from obtained from Taiyuan, Shanxi, China.
4. The seed of *Bixa orellana* was obtained from Kuala Lumpur, Malaysia.
5. The leaf of *Camellia sinensis* var *assamica* was obtained from Nantou, Taiwan.
6. The lemon of *Citrus depressa* Hayata was obtained from Pingtong, Taiwan.

General Experimental Procedures:
1. Quantitative analysis of major components of the water soluble nutrients and the lipid soluble nutrients by high performance liquid chromatography (HPLC).

To determine the contents of the major components to be extracted from a plant material using the process of the present disclosure, products prepared by the following Examples 1-6 were subjected to HPLC analysis using a Hitachi LaChrom HPLC System equipped with a 5410 UV detector, and a LaChromUltra C18 (2 μm) column (Hitachi) or a LaChrom C8 (5 μm) column (Hitachi) under the operating conditions shown in Tables 1 and 2.

TABLE 1

HPLC operating conditions for quantitative analysis of water soluble nutrients

| Operating conditions | Water soluble nutrients | | | | | |
|---|---|---|---|---|---|---|
| | Vitamin C | γ-Amino butyric acid | Salvianolic acid | Norbixin | Catechin | Citric acid |
| Column | C18 | C18 | C18 | C18 | C18 | C18 |
| Detection wavelength | 240 nm | 255 nm | 280 nm | 485 nm | 230 nm | 210 nm |
| Mobile phase A | methanol | acetonitrile | acetonitrile | acetonitrile | acetonitrile | methanol |
| B | 0.005M tetrabutyl ammonium hydroxide | 0.02M ammonium acetate buffer | 0.05% phosphate solution | 0.1% formic acid solution | 0.1% trifluoroacetic acid solution | acetonitrile |
| A:B (v/v) | 80:20 | 20:80 | 15:85 | 80:20 | 5:95 | 60:40 |
| Conditions for gradient elution | mobile phase A was maintained at 80% during 0-5 min, was increased from 80% to 100% at 5 min, and was maintained at 100% during 15-20 min | mobile phase A was maintained at 20% during 0-10 min, was increased from 20% to 100% during 10-30 min, was decreased from 100% to 20% at 30 min, and was maintained at 20% during 30-55 min | mobile phase A was maintained at 15% during 0-15 min, was increased from 15% to 50% at 15 min, was maintained at 50% during 15-35 min, and increased from 50% to 90% during 35-45 min | mobile phase A was maintained at 80% during 0-5 min, was increased from 80% to 95% during 5-15 min, was increased from 95% to 100% during 15-25 min, and was decreased from 100% to 85% during 25-35 min | mobile phase A was maintained at 5% during 0-3 min, was decreased from 5% to 3.5% at 3 min, was maintained at 3.5% during 3-18 min, was increased from 3.5% to 5% at 18 min, and was maintained at 5% during 18-23 min | mobile phase A was maintained at 60% during 0-10 min, was increased from 60% to 100% at 10 min, was maintained at 100% during 10-15 min, was decreased from 100% to 60% at 15 min, and was maintained at 60% during 15-20 min |
| Flow rate (mL/minute) | 1.0 | 1.2 | 0.9 | 0.4 | 0.5 | 1.0 |

TABLE 2

HPLC operating conditions for quantitative analysis of lipid soluble nutrients

| Operating conditions | Lipid soluble nutrients | | | | |
|---|---|---|---|---|---|
| | Vitamin E | Curcumin | Tashinone | Phytosterol | Chlorophyll |
| Column | C18 | C18 | C18 | C8 | C8 |
| Detection wavelength | 295 nm | 254 nm | 254 nm | 485 nm | 440 nm |
| Mobile phase A | acetonitrile | acetonitrile | methanol | methanol | methanol |
| Mobile phase B | water | 1% acetic acid solution | 0.5% acetic acid solution | acetone | acetonitrile and acetone (80:20, v/v) |
| A:B (v/v) | 95:5 | 55:45 | 80:20 | 75:25 | 100:0 |
| Conditions for gradient elution | mobile phase A was maintained at 95% during 0-10 min, was increased from 95% to 100% during 10-20 min, was decreased from 100% to 95% at 20 min, and was maintained at 95% during 20-25 min | mobile phase A was maintained at 55% during 0-10 min, was increased from 55% to 100% at 10 min, was maintained at 100% during 10-15 min, was decreased from 100% to 55% at 15 min, and was maintained at 55% during 15-25 min | mobile phase A was maintained at 80% during 0-10 min, was decreased from 80% to 50% at 10 min, was maintained at 50% during 10-25 min, was increased from 50% to 80% at 25 min, and was maintained at 80% during 25-30 min | mobile phase A was maintained at 75% during 0-5 min, was decreased from 75% to 50% at 5 min, was maintained at 50% during 5-25 min, was increased from 50% to 65% at 25 min, was maintained at 65% during 25-45 min, was increased from 65% to 75% at 45 min, and was maintained at 75% during 45-55 min | mobile phase A was maintained at 100% during 0-10 min, was decreased from 100% to 60% at 10 min, was maintained at 60% during 10-25 min, was increased from 60% to 100% at 25 min, and was maintained at 100% during 25-40 min |
| Flow rate (mL/minute) | 1.0 | 1.5 | 0.5 | 0.8 | 0.5 |

Example 1

Extracting the Water Soluble and Lipid Soluble Nutrients from Sea Buckthorn 100 g of pericarp and pulp of the berry of Sea Buckthorn (as a water soluble nutrient-based plant part) and 100 g of seed with the aril of the berry of Sea Buckthorn (as a lipid soluble nutrient-based plant part) were pulverized, so that a first pulverized plant part having an average particle size of 100 μm and a second pulverized plant part having an average particle size of 75 μm were respectively obtained. The water soluble nutrient and lipid soluble nutrient contained in these pulverized plant parts (see Table 3) are extracted by the following steps, and the operating conditions of the following steps are summarized in Table 4.

To be specific, the first pulverized plant part was subjected to a fractional distillation under an increasing temperature gradient at a pressure of 0.01~101.1 Kpa, so as to obtain a first residue, and a distillate. The distillate includes three separated distillate fractions, i.e., a first distillate fraction collected at a temperature of lower than 50° C., a second distillate fraction collected at a temperature of not less than 50° C. and lower than 70° C., and a third distillate fraction collected at a temperature ranging from 70° C. to 90° C.

The first, second and third distillate fractions thus collected were used to extract the lipid soluble nutrient in the second pulverized plant part. Specifically, the second pulverized plant part was firstly subjected to a first extraction, i.e., immersion of the second pulverized plant part in the first distillate fraction at 30° C. for 8 hours to form a first mixture followed by distillation of the first mixture at 50° C. for 2 hours, so as to obtain a second residue. The second residue formed in the first extraction was further subjected to a second extraction, i.e. immersion of the second residue in the second distillate fraction at 25° C. for 3 hours to form a second mixture followed by distillation of the second mixture at 60° C. for 2 hours, so as to obtain a third residue. Thereafter, the third residue formed in the second extraction was subjected to a third extraction, i.e. immersion of the third residue in the third distillate fraction at 30° C. for 4 hours to form a third mixture followed by distillation of the third mixture at 80° C. for 1.5 hours, so as to obtain a fourth residue. After extraction, the first residue and the fourth residue were mixed at 30° C. for 8 hours, followed by filtration to obtain a filtrate containing the water soluble nutrient and the lipid soluble nutrient.

Examples 2-6

Extracting the Water Soluble and Lipid Soluble Nutrients from Different Plant Materials In Examples 2-6, different plant materials were used to determine the nutrient extraction efficiency. The plant materials and the corresponding water soluble nutrient-based plant part and lipid soluble nutrient-based plant part used in these examples are respectively summarized in Table 3. The procedure in each of Examples 2 to 6 was similar to that of Example 1, except that the operating conditions for distillation, extraction and mixing are different. In addition, in Examples 5 to 6, prior to the fractional distillation, the first pulverized plant part was subject to fermentation. Moreover, in Example 6, the lemon has been squeezed to extract the juice therefrom. The detailed information for Examples 2 to 6 is listed in Table 4.

To evaluate the nutrient extraction efficiency, the first pulverized plant part, the second pulverized plant part, the first residue, the fourth residue and the filtrate in each of Examples 1-6 were respectively subjected to HPLC analysis as set forth in the section entitled "1. Quantitative analysis of major components of the water soluble nutrients and the lipid soluble nutrients by high performance liquid chromatography (HPLC)," of the General Experimental Procedures, so as to determine the nutrient contents thereof (see Table 4).

TABLE 3

Plant parts of the plant materials used in the examples and the major nutrient thereof

| | Example | | | | | |
|---|---|---|---|---|---|---|
| | 1 | 2 | 3 | 4 | 5 | 6 |
| Plant material | Berry of Sea Buckthorn | Rhizome of *Curcuma longa L.* | Root of *Salvia miltiorrhiza* | Seed of *Bixa orellana* | Leaf of *Camellia sinensis* var. *assamica* | Squeezed lemon of *Citrus deoressa Hayata* |
| Water soluble nutrient-based plant part | Pericarp and pulp | Main rhizome | Epidermis | Seed without the aril | Leaf without petiole and vein | Pericarp and pulp |
| Water soluble nutrient | Vitamin C | γ-Amino butyric acid | Salvianolic acid | Norbixin | Catechin | Citric acid |
| Lipid soluble nutrient-based plant part | Seed with the aril | Lateral shoots | Root without the epidermis | Aril | Petiole and vein | Seed with the aril |
| Lipid soluble nutrient | Vitamin E | Curcumin | Tashinone | Phytosterol | Chlorophyll | Vitamin E |

TABLE 4

Operating conditions for extracting the nutrients and the nutrient content determined in the given product

| | | Example | | | | | |
|---|---|---|---|---|---|---|---|
| | | 1 | 2 | 3 | 4 | 5 | 6 |
| First pulverized plant part | Average particle diameter (μm) | 100 | 125 | 125 | 75 | 75 | 125 |
| | Water soluble nutrient content (mg/100 g) | Vitamin C 295.6 ± 21.5 | γ-Amino butyric acid 88.9 ± 7.8 | Salvianolic acid 2578.5 ± 238.1 | Norbixin 2105.1 ± 184.3 | Catechin 196.4 ± 8.4 | Citric acid 214.4 ± 18.5 |
| Second pulverized plant part | Average particle diameter (μm) | 75 | 100 | 75 | 50 | 50 | 100 |
| | Lipid soluble nutrient content (mg/100 g) | Vitamin E 177.3 ± 12.9 | Curcumin 924.4 ± 84.5 | Tashinone 647.2 ± 58.4 | Phytosterol 57.2 ± 4.8 | Chlorophyll 14.7 ± 2.1 | Vitamin E 4.5 ± 0.3 |
| Fermentation | Temperature (° C.) | — | — | — | — | 40 | 25 |
| | Time (hr) | — | — | — | — | 120 | 360 |
| | Liquid portion obtained in the fermentation process (mg/100 g) | — | — | — | — | 28.2 ± 3.5 | 178.2 ± 15.5 |
| | Water soluble nutrient content (mg/100 g) | — | — | — | — | Catechin 16.2 ± 1.7 | Citric acid 131.5 ± 14.1 |
| | Lipid soluble nutrient content (mg/100 g) | — | — | — | — | Chlorophyll <0.001 | Vitamin E 2.2 ± 0.2 |
| First distillate fraction | Pressure (KPa) | 0.01-101.1 | 0.01-151.1 | 0.01-202.2 | 0.01-101.1 | 0.01-101.1 | 0.01-202.2 |
| | Temperature | lower than 50° C. | | | | | |
| Second distillate fraction | Pressure (KPa) | 0.01-101.1 | 0.01-151.1 | 0.01-202.2 | 0.01-101.1 | 0.01-101.1 | 0.01-202.2 |
| | Temperature | Not less than 50° C. and lower than 70° C. | | | | | |
| Third distillate | Pressure (KPa) | 0.01-101.1 | 0.01-151.1 | 0.01-202.2 | 0.01-101.1 | 0.01-101.1 | 0.01-202.2 |

TABLE 4-continued

Operating conditions for extracting the nutrients and the nutrient content determined in the given product

| | | | Example | | | | | |
|---|---|---|---|---|---|---|---|---|
| | | | 1 | 2 | 3 | 4 | 5 | 6 |
| fraction | Temperature | | | | 70° C. to 90° C. | | | |
| First residue | Liquid portion | Water soluble nutrient content (mg/100 g) | Vitamin C 267.2 ± 13.2 | γ-Amino butyric acid 20.2 ± 3.2 | Salvianolic acid 1801.4 ± 98.5 | Norbixin 51.7 ± 5.6 | Catechin 102.2 ± 9.7 | Citric acid 455.2 ± 43.6 |
| | | Lipid soluble nutrient content (mg/100 g) | Vitamin E 64.2 ± 6.5 | Curcumin 383.5 ± 36.5 | Tashinone 554.3 ± 31.8 | Phytosterol 197.7 ± 18.5 | Chlorophyll 4.2 ± 0.3 | Vitamin E 14.2 ± 1.4 |
| First extraction | Immersion temperature/time | | 30° C. 8 hrs | 25° C. 30 hrs | 5° C. 48 hrs | 25° C. 18 hrs | 20° C. 18 hrs | 40° C. 2 hrs |
| | Distillation temperature/time | | 50° C. 2 hrs | 50° C. 5 hrs | 40° C. 2 hrs | 40° C. 2.5 hrs | 40° C. 1 hr | 60° C. 5 hrs |
| Second extraction | Immersion temperature/time | | 25° C. 3 hrs | 30° C. 4 hrs | 15° C. 8 hrs | 50° C. 1 hr | 20° C. 12 hrs | 60° C. 12 hrs |
| | Distillation temperature/time | | 60° C. 2 hrs | 75° C. 3 hrs | 50° C. 0.5 hrs | 60° C. 1.5 hrs | 60° C. 4 hrs | 70° C. 5 hrs |
| Third extraction | Immersion temperature/time | | 30° C. 4 hrs | 30° C. 6 hrs | 40° C. 4 hrs | 75° C. 1 hr | 50° C. 6 hrs | 75° C. 2 hrs |
| | Distillation temperature/time | | 80° C. 1.5 hrs | 85° C. 0.5 hrs | 75° C. 3 hrs | 90° C. 1.5 hrs | 80° C. 3 hrs | 90° C. 2 hrs |
| Fourth residue | Liquid portion | Water soluble nutrient content (mg/100 g) | Vitamin C 3.5 ± 0.2 | γ-Amino butyric acid 48.5 ± 4.3 | salvianolic acid 2930.5 ± 211.5 | Norbixin 1355.2 ± 134.9 | Catechin 38.5 ± 3.7 | Citric acid 43.5 ± 4.3 |
| | | Lipid soluble nutrient content (mg/100 g) | Vitamin E 136.8 ± 11.2 | Curcumin 1236.5 ± 93.5 | Tashinone 24.2 ± 2.6 | Phytosterol 17.7 ± 1.6 | Chlorophyll 2.1 ± 0.4 | Vitamin E 66.4 ± 6.2 |
| Mixing | Temperature (° C.) | | 30 | 25 | 5 | 30 | 40 | 50 |
| | Time (hr) | | 8 | 15 | 48 | 12 | 4 | 24 |
| Filtrate | Water soluble nutrient content (mg/100 g) | | Vitamin C 261.5 ± 24.7 | γ-Amino butyric acid 63.5 ± 5.8 | Salvianolic acid 3647.5 ± 289.7 | Norbixin 1388.4 ± 128.5 | Catechin 141.1 ± 12.5 | Citric acid 490.6 ± 48.2 |
| | Lipid soluble nutrient content (mg/100 g) | | Vitamin E 186.0 ± 17.7 | Curcumin 1568.0 ± 110.4 | Tashinone 567.5 ± 48.5 | Phytosterol 201.5 ± 18.5 | Chlorophyll 5.8 ± 0.5 | Vitamin E 76.8 ± 8.0 |

As shown in Table 4, the distillate obtained by distilling the first pulverized plant part can be used to effectively extract the nutrients (especially the lipid soluble nutrient) from the second pulverized plant part. Thus, the method of the disclosure does not require any industrial solvents for extracting the water soluble and lipid soluble nutrients. In other words, the water soluble and lipid soluble nutrients contained in the plant can be extracted naturally and safely, and can be easily formulated into any functional food or health product for humans.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding various inventive aspects.

While the disclosure has been described in connection with what is considered the exemplary embodiments, it is understood that this disclosure is not limited to the disclosed embodiment but is intended to cover various arrangements included within the spirit and scope of the broadest interpretation so as to encompass all such modifications and equivalent arrangements.

What is claimed is:

1. A method of extracting nutrients from a plant, comprising:
   (a) pulverizing a first plant material of the plant so as to obtain a first pulverized plant part containing a water-soluble nutrient and a plant juice;
   (b) pulverizing a second plant material so as to obtain a second pulverized plant part containing a lipid-soluble nutrient;

(c) subjecting the first pulverized plant part to a fractional distillation under an increasing temperature gradient at a pressure in a range from 0.01 kPa to 202.2 kPa to obtain a liquid distillate fraction and a first residue that contains a water-soluble nutrient,
wherein the distillate includes three separated distillate fractions: a first distillate fraction collected at a temperature of lower than 50° C., a second distillate fraction collected at a temperature ranging from 50° C. to 70° C., and a third distillate fraction collected at a temperature ranging from 70° C. to 90° C.; and
(d) immersing the second pulverized plant part in a liquid distillate fraction at a temperature in a range from 5° C. to 75° C. for 1 hour to 48 hours to form a mixture followed by distilling the mixture at a temperature in a range from 40° C. to 90° C. for 0.5 hours to 10 hours to obtain a second residue that is a second extract that contains the lipid-soluble nutrient,
wherein the water-soluble nutrient is selected from the group consisting of vitamin C, γ-aminobutyric acid, salvianolic acid, norbixin, catechin, citric acid, anthocyanidin, and combinations thereof, and
wherein the lipid-soluble nutrient is selected from the group consisting of vitamin E, curcumin, tashinone, phytosterol, chlorophyll, and combinations thereof.

2. The method of claim 1, wherein the first plant material and the second plant material are the same plant material.

3. The method of claim 2, wherein the first and second plant materials are each independently selected from the group consisting of root, stem, leaf, seed, and fruit.

4. The method of claim 2, wherein the first and the second plant materials are derived from different parts of the plant.

5. The method of claim 1, further comprising a step of fermenting the first pulverized plant part before the distilling of the first pulverized plant part.

6. The method of claim 1, further comprising a step of mixing the first residue and the second residue followed by filtration to obtain a filtrate containing the water-soluble nutrient and the lipid-soluble nutrient.

7. The method of claim 6, wherein the mixing step is conducted at a temperature ranging from 5° C. to 50° C. for 4 hours to 120 hours.

8. The method of claim 1, wherein, in step (d), the second pulverized plant part is immersed in the first distillate fraction to obtain a first mixture.

9. The method of claim 8, wherein the immersing of the second pulverized plant part in the first distillate fraction is conducted for 2 hours to 48 hours, and the first mixture is distilled for 0.5 hours to 10 hours.

10. The method of claim 8, wherein the immersing of the second pulverized plant part in the first distillate fraction is conducted at a temperature in a range from 5° C. to 40° C., and the first mixture is distilled at a temperature in a range from 40° C. to 70° C.

11. The method of claim 8, further comprising step of immersing the second residue in the second distillate fraction to form a second mixture followed by distilling the second mixture, so as to obtain a third residue that contains a lipid-soluble nutrient.

12. The method of claim 11, wherein the step of immersing the second residue in the second distillate fraction is conducted for 1 hour to 48 hours, and the distilling of the second mixture is conducted for 0.5 hours to 6 hours.

13. The method of claim 11, wherein the step of immersing the second residue in the second distillate fraction is conducted at a temperature ranging from 5° C. to 60° C., and the distilling of the second mixture is conducted at a temperature ranging from 50° C. to 80° C.

14. The method of claim 11, further comprising a step of immersing the third residue in the third distillate fraction to form a third mixture followed by distilling the third mixture to obtain a fourth residue that contains a lipid-soluble nutrient.

15. The method of claim 14, wherein the step of immersing the third residue in the third distillate fraction is conducted for 1 hour to 12 hours, and the distilling of the third mixture is conducted for 0.5 hours to 6 hours.

16. The method of claim 14, wherein the step of immersing the third residue in the third distillate fraction is conducted at a temperature ranging from 20° C. to 75° C., and the distilling of the third mixture is conducted at a temperature ranging from 60° C. to 90° C.

17. The method of claim 14, further comprising a step of mixing the first residue and the fourth residue followed by filtration to obtain a filtrate containing the water-soluble nutrient and the lipid-soluble nutrient.

* * * * *